United States Patent [19]

Scafidi

[11] Patent Number: 5,683,683
[45] Date of Patent: Nov. 4, 1997

[54] BODY WASH COMPOSITION TO IMPART CONDITIONING PROPERTIES TO SKIN

[75] Inventor: Anthony A. Scafidi, Westchester, Ill.

[73] Assignee: Helene Curtis, Inc., Chicago, Ill.

[21] Appl. No.: 531,712

[22] Filed: Sep. 21, 1995

[51] Int. Cl.⁶ .............................. A61K 7/48; A61K 7/50
[52] U.S. Cl. .................... 424/70.19; 424/70.28; 514/846; 252/DIG. 5
[58] Field of Search ................ 424/70.11, 401, 424/70.19, 78.03, 70.28; 514/846; 252/DIG. 5

[56] References Cited

U.S. PATENT DOCUMENTS

| | | | |
|---|---|---|---|
| 4,061,602 | 12/1977 | Oberstar et al. | 252/547 |
| 4,209,449 | 6/1980 | Mayhew et al. | 260/403 |
| 5,085,857 | 2/1992 | Reid et al. | 424/70 |
| 5,135,748 | 8/1992 | Ziegler et al. | 424/401 |
| 5,358,667 | 10/1994 | Bergmenn | 252/547 |
| 5,456,863 | 10/1995 | Bergmann | 252/547 |

FOREIGN PATENT DOCUMENTS 0 511 652  4/1992  European Pat. Off. .

OTHER PUBLICATIONS

Fost, "Multifunctional biomimetic phospholipids: their applications in personal car," *Cosmetics and Toiletries Manufacture Worldwide*, (1994), pp. 83–89.

Technical Bulletin, No. 1016b, (January, 1993), Mona Industries, Paterson, NJ.

Technical Bulletin, No. 1018a, (January, 1993), Mona Industries, Paterson, NJ.

Technical Bulletin, No. 1019a, (January, 1993), Mona Industries, Paterson, NJ.

Technical Bulletin, No. 1057, (May, 1994), Mona Industries, Paterson, NJ.

Product Label, "Oil of Olay Moisturizing Body Wash," Procter & Gamble, Cincinnati, Ohio (1993).

*Primary Examiner*—Sallie M. Gardner
*Attorney, Agent, or Firm*—Milton L. Honig

[57] ABSTRACT

A body wash composition containing an anionic cleansing surfactant, such as an alkyl ether sulfate or an alkyl sulfate, like sodium lauryl ether sulfate or sodium lauryl sulfate; a polymeric cationic conditioning compound, such as a quaternized guar gum; and a quaternized phosphate ester in an aqueous carrier is disclosed. The composition is used in a method to cleanse the skin and to impart conditioning properties to the skin.

30 Claims, No Drawings

BODY WASH COMPOSITION TO IMPART CONDITIONING PROPERTIES TO SKIN

FIELD OF INVENTION

The present invention relates to a body wash composition and to a method of treating skin that cleanses and imparts conditioning properties to the skin. More particularly, the present invention is directed to a body wash composition comprising: (a) an anionic surfactant, like an alkyl ether sulfate, such as sodium lauryl ether sulfate; (b) a polymeric cationic conditioning compound, such as a quaternized guar gum; and (c) a quaternized phosphate ester, in an aqueous carrier. The body wash compositions of the present invention exhibit a minimal interaction, if any, between the cationic components and the anionic components, making the anionic components and the cationic components available to effectively cleanse and condition the skin.

BACKGROUND OF THE INVENTION

Individuals buy and use a skin cleanser, either in a bar or liquid form, primarily for its cleansing properties. However, skin cleansers often dry the skin because protective oils are removed from the skin during the cleansing process. The consumer, therefore, desires a skin cleanser that leaves the skin in a cosmetically satisfactory condition.

Present-day skin cleansers often are formulated with highly effective soaps and synthetic surfactants, particularly anionic surfactants, that effectively cleanse the skin. However, after washing, the skin can be left in a cosmetically unsatisfactory state because soap and anionic surfactant-based skin cleansers not only remove the dirt and soil from the skin, but also remove oils that are naturally present on the surface of the skin. Therefore, the properties of anionic surfactants that effectively cleanse the skin also serve to leave the skin in a cosmetically unsatisfactory condition. Nonionic and amphoteric surfactants are less irritating to the skin than anionic surfactants, but are not as effective in cleansing the skin. To strike a balance between cleansing the skin and leaving the skin in a cosmetically satisfactory condition, present-day liquid skin cleansers typically are based on nonionic or amphoteric surfactants.

Accordingly, skin that has been repeatedly washed with an anionic surfactant-based skin cleanser, or a soap, often requires treatment with a skin-conditioning composition to replenish the oil and moisture removed from the skin, and to generally improve the unsatisfactory physical and cosmetic condition of the skin. Conditioning compositions, such as hand creams or lotions, normally are applied after washing, and can be gel or a cream-like in consistency and contain oils. Therefore, investigators have sought body wash compositions that both cleanse the skin and leave the skin in a cosmetically satisfactory state, such that the subsequent treatment with a conditioner composition can be reduced or avoided.

Investigations directed at providing a composition that behaves both as a skin cleanser and as a skin conditioner yielded compositions that possessed several disadvantages. Investigators, therefore, attempted to combine anionic surfactants with cationic conditioners.

It is known in the art that anionic surfactants are suitable for cleansing the skin, and that, in many instances, cationic surfactants and cationic polymers are suitable skin conditioners. However, the major difficulty encountered by investigators is the inherent incompatibility between an anionic surfactant and a cationic surfactant or cationic polymer. Contact between the anionic surfactant and the cationic surfactant or cationic polymer either produces an intractable precipitate that forms immediately, or causes an interaction between the anionic and cationic components that significantly reduces their respective cleansing and conditioning properties. The reduction in cleansing and conditioning effectiveness also is observed in compositions wherein the anionic and cationic components do not precipitate from the composition, but remain in solution or in a suspended state.

This incompatibility between an anionic compound and a cationic compound is well recognized by workers skilled in the art. For example, Sagarin, in *Cosmetics*, Interscience Publishers, Inc., New York, p. 538, (1957), discloses that anionic and cationic compounds cannot be used in combination because they react to form insoluble salts. Investigators, therefore, have combined conditioners with nonionic or amphoteric surfactants to overcome this incompatibility problem. However, this advantage was offset by the relatively poor cleaning ability of a nonionic or amphoteric surfactant compared to an anionic surfactant.

Preferred body wash compositions, therefore, are anionic in character. The incorporation of a cationic conditioning compound into an anionic body wash composition ranges from difficult to impossible because of the inherent incompatibility between anionic and cationic surfactants. Nevertheless, such a composition is desirable because of the convenience such a combination product offers to the consumer. In such a product, the anionic surfactant acts to rid the skin of dirt, surface film, debris, and the like, while the cationic compound deposits on the skin to provide conditioning benefits. However, until the composition and method of the present invention, it has proven very difficult to provide a stable anionic surfactant-based composition because of the inherent incompatibility between cationic and anionic surfactants.

Consequently, and in accordance with an important feature of the present invention, a polymeric cationic conditioning compound and a cationic conditioning surfactant, i.e., a quaternized phosphate ester, are incorporated into a composition wherein an interaction between the anionic and cationic components of the composition is essentially precluded. The body wash composition then is utilized to clean the skin, and, simultaneously, to impart conditioning properties to the skin.

The need for an effective and stable body wash composition that cleanses and conditions the skin in a single treatment has long been recognized in the art. Some body wash compositions are specially formulated for mildness, and, accordingly, low detergency, in order to leave a portion of the natural oils on the skin. The present invention is directed to a body wash composition that also effectively cleanses the skin.

Therefore, the present invention relates to a body wash composition for cleansing and imparting improved physical and cosmetic properties to the skin. In accordance with the present invention, anionic surfactants can be combined with a polymeric cationic conditioning compound and a quaternized phosphate ester to provide a stable and effective body wash composition. As manufactured, the composition is metastable, wherein the term "metastable composition" is defined as a composition that is sufficiently stable to resist phase separation during storage and essentially precludes an interaction between the cationic and anionic components of the composition; but, upon application to the skin, deposits a substantial amount of the cationic components onto the skin. It also has been found that the optional addition of other conditioning agents, like oils, to the body wash composition of the present invention further improves the conditioning properties imparted to the skin.

More particularly, it has been found that a polymeric cationic conditioning compound and a cationic quaternized phosphate ester, when incorporated into a body wash composition including a nonsubstantive anionic surfactant and an optional oil, provide a body wash composition that generates sufficient foaming and thoroughly cleanses the skin, in addition to depositing a sufficient amount of the cationic polymer, the quaternized phosphate ester, and optional oil onto the skin to condition the skin. Such results are unexpected in the art because anionic surfactants, as a class, are essentially incompatible with cationic compounds. The compatibility demonstrated by the combination of the anionic surfactant and the quaternized phosphate ester and the cationic conditioning polymer utilized in the present invention permits sufficient deposition of the substantive cationic conditioning components onto the skin, while the anionic surfactant cleanses the skin.

The present invention is directed to a body wash composition comprising a nonsubstantive and high-foaming anionic surfactant and a combination of substantive cationic conditioning components, that simultaneously cleanses and imparts desirable physical and cosmetic properties to the skin. In contrast to the prior art, wherein cationic polymers were blended primarily with amphoteric surfactants, the body wash composition of the present invention comprises a cationic polymer, a quaternized phosphate ester, an optional oil, and an anionic surfactant to cleanse and condition the skin. Therefore, the stability and incompatibility problems normally encountered when a cationic surfactant and anionic surfactant are present in the same composition have been overcome.

SUMMARY OF THE INVENTION

The present invention is directed to a composition and method of cleansing and conditioning skin. More particularly, the present invention is directed to a method of treating the skin, whereby the skin is cleansed and conditioned, simultaneously, by contacting the skin with a body wash composition comprising an anionic surfactant, a polymeric cationic conditioning compound, and a quaternized phosphate ester in an aqueous carrier. Optionally, an oil, like castor oil, or an amphoteric surfactant, like a betaine or a hydroxysultaine, or a nonionic surfactant, like an alkanolamide, can be included in the composition to improve the esthetic properties and consumer appeal of the composition. Consequently, treating the skin with single application of an aqueous composition including an anionic surfactant, such as an alkyl ether sulfate, like sodium lauryl ether sulfate; a polymeric cationic conditioning compound, like a quaternized guar gum; a quaternized phosphate ester, such as a $C_8$-$C_{22}$ alkamidopropyl phosphatidyl PG-dimonium chloride, and, optionally, an oil, like castor oil, effectively cleanses the skin and simultaneously imparts conditioning properties to the skin.

Therefore, one aspect of the present invention is to provide a body wash composition that cleanses the skin and that imparts improved physical and cosmetic properties to the skin in a single application.

Another aspect of the present invention is to provide a body wash composition comprising an anionic surfactant, a polymeric cationic conditioning compound, a quaternized phosphate ester, and, optionally, an oil, an amphoteric surfactant, a nonionic surfactant, or a combination thereof, in an aqueous carrier.

Another aspect of the present invention is to provide a method of treating skin with a body wash composition to simultaneously cleanse and condition the skin with a single application of the composition to the skin.

Yet another aspect of the present invention is to provide a method of treating skin to yield cleansed and conditioned skin by contacting the skin with an aqueous composition comprising about 1% to about 40% by weight of an anionic surfactant, about 0.01% to about 2% by weight of a polymeric cationic conditioning compound, and about 0.01% to about 5% by weight of a quaternized phosphate ester.

Another aspect of the present invention is to provide a method of treating skin to yield cleansed, conditioned skin by contacting the skin with an aqueous composition comprising about 1% to about 40% by weight of an anionic surfactant, from about 0.01% to about 2% by weight of a polymeric cationic conditioning compound, about 0.01% to about 5% by weight of a quaternized phosphate triester, and, optionally, 0% to about 4% by weight of an oil, such as castor oil, 0% to about 5% by weight of an amphoteric surfactant, such as betaine or a hydroxypropylsultaine, and 0% to about 10% by weight of a nonionic surfactant, like an alkanolamide, or combinations thereof.

Another aspect of the present invention is to provide a method of treating skin to yield, in a single treatment, cleansed and well-conditioned skin by contacting the skin with an aqueous composition comprising about 1% to about 40% by weight of an anionic surfactant, about 0.01% to about 2% by weight of quaternized guar gum as the polymeric cationic conditioning compound, about 0.01% to about 5% by weight of stearamidopropyl phosphatidyl PG-dimonium chloride, as the cationic conditioning surfactant, and 0% to about 2% by weight of castor oil.

These and other aspects and advantages of the present invention will become apparent from the following detailed description of the preferred embodiments.

DETAILED DESCRIPTION OF THE PREFERRED EMBODIMENTS

A body wash composition of the present invention comprises an anionic surfactant, a polymeric cationic conditioning compound, and a quaternized phosphate ester, in an aqueous carrier. In accordance with an important feature of the present invention, the body wash composition includes an anionic surfactant and substantive cationic conditioning agents to both cleanse and condition the skin in a single application of the composition to the skin. Surprisingly and unexpectedly, the body wash composition demonstrates excellent stability with respect to resisting phase separation, and with respect to resisting interaction between the anionic and cationic components, thereby avoiding the necessity of including an amphoteric or nonionic surfactant in the composition. Optionally, however, an amphoteric surfactant, a nonionic surfactant or a combination thereof, can be included in the composition to impart improved physical properties, and, therefore, enhanced consumer appeal to the composition. Furthermore, an oil can be optionally included in the composition to enhance skin conditioning.

The anionic surfactant used in the composition and method of the present invention includes any of the anionic surfactants known or previously used in the art of skin cleansers. However, an anionic surfactant is a necessary ingredient in the composition of the present invention because it effectively cleanses the skin and generates a high, stable foam level that consumers equate with cleaning efficiency. Nonionic and amphoteric surfactants generally are not as effective in cleansing the skin and do not provide the high foam level desired by consumers. Therefore, nonionic and amphoteric surfactants are unsatisfactory as the primary cleansing surfactant in a composition of the present invention. However, optionally, nonionic or amphoteric surfactants can be included in a composition of the present invention to help increase and stabilize foam, to provide a suitable viscosity, or to provide other functional or esthetic properties to the composition.

Usually, the anionic surfactant includes a hydrophobic moiety, such as a carbon chain including about 8 to about 30 carbon atoms, and particularly about 12 to about 20 carbon atoms, and further includes a hydrophilic moiety, such as sulfate, sulfonate, carbonate, phosphate, or carboxylate. Often, the hydrophobic carbon chain is etherified, such as with ethylene oxide or propylene oxide, to impart a particular physical property, such as increased water solubility or reduced surface tension to the anionic surfactant.

The anionic surfactants are well known and have been widely used in the art of skin cleansers. Therefore, suitable anionic surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta-alkyloxy alkane sulfonates, alkylarylsulfonates, alkyl monoglyceride sulfates, alkyl monoglyceride sulfonates, alkyl carbonates, alkyl ether carboxylates, fatty acids, sulfosuccinates, sarcosinates, octoxynol or nonoxynol phosphates, taurates, fatty taurides, fatty acid amido polyoxyethylene sulfates, isothionates, or mixtures thereof. Additional anionic cleansing surfactants are listed in McCUTCHEON'S EMULSIFIERS AND DETERGENTS, 1993 ANNUALS, McCutcheon Division, MC Publishing Co., Glen Rock, N.J., pages 263-266, incorporated herein by reference. Numerous other anionic surfactants, and classes of anionic surfactants, are disclosed in Laughlin et al. U.S. Pat. No. 3,929,678, incorporated herein by reference.

Usually, the anionic surfactant is present in the composition as a neutralized salt in the form of a sodium, potassium, lithium, ammonium, alkylammonium or hydroxyalkylammonium salt, wherein the alkyl or hydroxyalkyl moiety has 1 to about 3 carbon atoms. The alkyl sulfates and alkyl ether sulfates are particularly effective classes of anionic surfactants. Examples of anionic surfactants useful in the composition and method of the present invention include, but are not limited to, the ammonium, monoethanolamine, diethanolamine, triethanolamine, isopropylamine, sodium, potassium, lithium, and magnesium salts of lauryl sulfate, dodecylbenzenesulfonate, lauryl sulfosuccinate, lauryl ether sulfate, lauryl ether carboxylate, lauryl sarcosinate, cocomethyl tauride, and sulfosuccinate half ester amide, or combinations thereof. Examples of especially useful anionic surfactants are a lauryl sulfate salt, a lauryl ether sulfate salt, and mixtures thereof.

In accordance with an important feature of the present invention, the anionic surfactant is present in the composition in an amount of about 1% to about 40%, and preferably about 5% to about 35%, by weight of the composition. To achieve the full advantage of the present invention, the body wash composition contains about 8% to about 30% by weight anionic surfactants.

If the anionic surfactant is present in an amount of less than about 1% by weight of the composition, then the skin is not sufficiently cleansed when contacted with a composition of the present invention. Furthermore, if the anionic surfactant is present in amounts greater than about 40% by weight of the composition, greater cleansing efficacy is not demonstrated, and the amount of anionic surfactant above about 40% by weight is wasted. It should be understood, however, that the anionic surfactant can be present in amounts greater than about 40% by weight without adversely affecting the physical, esthetic, or functional properties of the body wash composition.

In accordance with another important feature of the present invention, the body wash composition includes a polymeric cationic conditioning compound that is substantive and imparts conditioning properties to skin. Both synthetic and naturally derived polymers having a quaternized nitrogen atom are useful in the composition and method of the present invention. Such useful cationic polymers have a weight average molecular weight of at least 100,000, and preferably at least 200,000, and up to about 1,000,000. A preferred weight average molecular weight is from about 250,000 to about 750,000.

Examples of synthetic quaternized polymers include, but are not limited to, polyquaternium-1, polyquaternium-2, polyquaternium-5, polyquaternium-6, polyquaternium-7, polyquaternium-8, polyquaternium-9, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22, polyquaternium-27, polyquaternium-28, polyquaternium-29, polyquaternium-30, and mixtures thereof, wherein the compound designation is the name adopted for the compound by the Cosmetic, Toiletry and Fragrance Association, and found in the *CTFA International Cosmetic Ingredient Dictionary*, J. Nikitakis, ed., Cosmetic, Toiletry and Fragrance Association, Inc., Washington, D.C. (1991).

The naturally derived quaternized polymers are especially useful in the composition and method of the present invention. Examples of the quaternized naturally derived polymers include, but are not limited to compounds designed in *The CTFA International Dictionary* as polyquaternium-4, polyquaternium-10, polyquaternium-24, guar hydroxypropyltrimonium chloride, cocodimonium hydroxypropyl hydrolyzed rice protein, stearyldimonium hydroxypropyl hydrolyzed rice protein, hydroxypropyltrimonium hydrolyzed silk, cocodimonium hydroxypropyl hydrolyzed soy protein, lauryldimonium hydroxypropyl hydrolyzed soy protein, hydroxypropyltrimonium hydrolyzed soy protein, hydroxypropyltrimonium hydrolyzed vegetable protein, stearyldimonium hydroxypropyl hydrolyzed vegetable protein, cocodimonium hydroxypropyl hydrolyzed wheat protein, hydroxypropyltrimonium hydrolyzed wheat protein, stearyldimonium hydroxypropyl hydrolyzed wheat protein, and mixtures thereof. In addition, the synthetic and the naturally derived quaternized polymers can be used in combination.

An especially useful quaternized polymer is guar hydroxypropyltrimonium chloride, and sold commercially under the tradename HI-CARE 1000, by Rhone-Poulenc, Crambury, N.J. Other commercially available quaternized guar-based conditioning agents include JAGUAR C-162, JAGUAR C-138, JAGUAR C-145, and JAGUAR C-17, from Rhone-Poulenc, Cranbury, N.J. Useful quaternized cellulosic compounds include, but are not limited to, CELQUAT SC-240 (polyquaternium-10) and CELQUAT L200 (polyquaternium-4), from National Starch and Chemical Corp., Bridgewater, N.J. and QUATRISOFT LM-200 (polyquaternium-24) from Amerchol Corp., Edison, N.J.

The polymeric cationic conditioning compound is present in the composition of the present invention in an amount of about 0.01% to about 2%, and preferably about 0.05% to about 1%, by weight of the composition. To achieve the full advantage of the present invention, the cationic polymeric conditioning compound is included in the body wash composition in an amount of about 0.05% to about 0.8% by weight of the composition. When the polymeric cationic conditioning compound is present in an amount above about 2% by weight of the composition, composition esthetics are adversely affected. Therefore, in accordance with an important feature of the present invention, the composition includes 2% or less, and preferably less than 1%, by weight of the polymeric cationic conditioning compound. It has been demonstrated that this amount of polymeric cationic conditioning compound, i.e., about 0.01% to about 2%, and preferably about 0.05% to about 1%, by weight, is sufficiently high to provide a stable composition and to impart conditioning properties to the skin.

The cationic polymer is an essential ingredient. Compositions including only a nonsubstantive, nonionic polymer, like hydroxypropylcellulose, as opposed to a quaternized guar gum, do not impart conditioning properties to skin. In contrast, the polymeric cationic conditioning compound included in the present composition is substantive to the skin, and also helps stabilize the composition by effectively preventing interaction between the anionic surfactant and the quaternized phosphate ester, and by providing a composition that resists phase separation under normal storage conditions. The polymeric cationic conditioning compound, present in a low amount of about 0.01% to about 2% by weight of the composition, imparts conditioning properties to the skin.

In addition to the anionic surfactant and the polymeric cationic conditioning compound, the body wash composition also includes a quaternized phosphate ester in an amount of about 0.01% to about 5%, and preferably from about 0.05% to about 2%, by weight of the composition to impart conditioning properties to skin. To achieve the full advantage of the present invention, the body wash composition contains about 0.1% to about 1% by weight of the quaternized phosphate ester.

In general, cationic surfactants are incompatible with anionic surfactants. However, the quaternized phosphate esters included in a composition of the present invention minimally interact, if at all, with the anionic surfactant present in the composition. Therefore, the anionic surfactant is available to cleanse the skin and the quaternized phosphate ester is available to condition the skin.

In particular, introducing quaternized phosphate ester into the composition: (1) provides an excellent conditioner for treating skin, and (2) surprisingly does not destabilize the composition to such a degree that an adverse interaction between the anionic surfactant and the quaternized phosphate ester occurs. Therefore, neither ingredient precipitation nor decreased product performance is observed. However, it has been theorized that introducing the quaternized phosphate ester into the composition does destabilize the composition to a slight, but desirable, degree. Accordingly, the quaternized phosphate ester is not completely soluble in the metastable composition, but is available for deposition onto skin upon skin contact, and resists removal from the skin during rinsing of the anionic surfactant from the skin.

Quaternized phosphate esters useful in the present invention have a phosphate ester moiety and a long carbon chain substituent, preferably having a carbonyl moiety, like an amide moiety. These quaternized phosphate esters demonstrate exceptional compatibility with the anionic surfactant when incorporated into a body wash composition of the present invention. It has been theorized, but is not relied upon herein, that these quaternized phosphate esters are sufficiently hydrophilic to provide a composition having the desired degree of stability to resist phase separation and yet are available to deposit on the skin.

The quaternized phosphate esters are depicted in general structural formula (I):

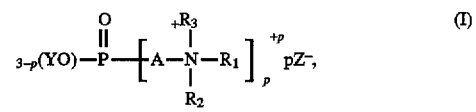

wherein $R_1$ is an alkyl chain having 8 to 26 carbon atoms, or $R_1$ is an alkamidoalkyl group having the structure

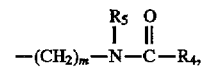

wherein $R_4$ is an aryl group, an alkaryl group, a saturated or unsaturated alkyl group, or a saturated or unsaturated hydroxyalkyl group wherein the alkyl or hydroxyalkyl group has about 7 to about 21 carbon atoms; $R_5$ is hydrogen, or an alkyl or a hydroxyalkyl group having 1 to about 6 carbon atoms; m is a numeral 1 to about 10; $R_2$ and $R_3$, independently, are an alkyl or a hydroxyalkyl group having 1 to about 6 carbon atoms; A is a residue of a glycol or a triol having 2 to about 4 carbon atoms, such as, for example, the residue of propylene glycol (i.e., —$OCH_2CH(OH)CH_2$— or ethylene glycol —$OCH_2OH_2$—); Z is an anion selected from the group consisting of chloride, bromide, methosulfate, ethosulfate, and mixtures thereof; Y is selected from the group consisting of hydrogen, an alkyl group, a hydroxyalkyl group, and an aryl group, either substituted or unsubstituted, wherein the alkyl or the hydroxyalkyl group has 1 to about 22 carbon atoms; and p is a numeral 1 to 3. To achieve the full advantage of the present invention, the quaternized phosphate ester of structural formula (I) is a quaternized phosphate triester that includes an alkamidopropyl moiety, like stearamidopropyl, as the $R_1$ substituent of the compound. For example, the quaternized phosphate ester of general structural formula (I) that includes an alkamidopropyl moiety as the $R_6$ substituent and wherein p is 3.

In addition, alkylhydroxyethyl phosphatidyl PG-imidazolinium chlorides having the structure (II)

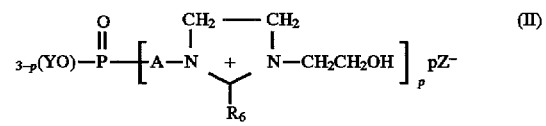

and alkampho phosphatidyl PG-glycinates having the structure (III):

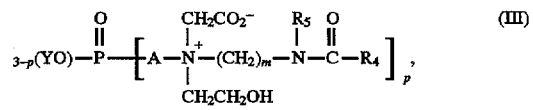

wherein $R_6$ is an alkyl group having about 5 to about 21 carbon atoms and all other terms are as defined above, are useful quaternized phosphate esters.

The alkamidopropyl moiety helps the quaternized phosphate ester impart conditioning properties to the skin. An example of an especially useful quaternized phosphate ester is the triester depicted in structural formula (IV), available commercially under the brandname PHOSPHOLIPID SV, from Mona Industries, Paterson, N.J., and having the CTFA Dictionary designation of

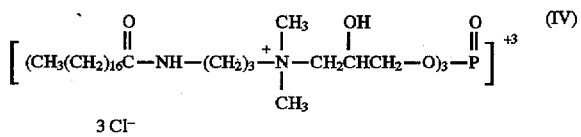

stearamidopropyl phosphatidyl PG-dimonium chloride. This particular compound has p equal to 3 and includes the alkyl moiety of stearic acid as a component of the amido substituent $R_1$.

It should be understood that the monophosphate ester (i.e., p=1) and diphosphate ester (i.e., p=2) of the quaternized phosphate ester illustrated in general structural formula (I) also can be used in the composition of the present invention as long as the basic properties of the body wash composition are not adversely affected. For example, suitable monophosphate and diphosphate esters of general structural formula (I) include Y as hydrogen, if the composition pH is sufficiently low such that the acid form of the phosphoric acid ester is present, as opposed to the neutralized, salt form; or Y is an alkyl group, a hydroxyalkyl group, or an aryl group.

Various quaternized phosphate esters of structural formula (I) are disclosed in Mayhew et al. U.S. Pat. No. 4,209,449, incorporated herein by reference. Other useful quaternized phosphate esters of structural formula (I) are available commercially from Mona Industries, Paterson, N.J., under the PHOSPHOLIPID tradename. Useful commercially available products include, but are not limited to, PHOSPHOLIPID SV, PHOSPHOLIPID EFA, PHOSPHOLIPID CDM, and PHOSPHOLIPID PTC. These compounds have the CTFA designations stearamidopropyl phosphatidyl PG-dimonium chloride, linoleamidopropyl phosphatidyl PG-dimonium chloride, coco phosphatidyl PG-dimonium chloride, and cocamidopropyl phosphatidyl PG-dimonium chloride, respectively. Other useful quaternized phosphate esters are borageamidopropyl phosphatidyl PG-dimonium chloride, laurampho phosphatidyl PG-glycinate, and cocohydroxyethyl phosphatidyl PG-imidazolinium chloride.

In addition to the above-described essential ingredients, other common cosmetic components and additives can be included in the composition of the present invention, as long as the basic properties of the body wash composition are not adversely affected. Such optional cosmetic components and additives include, but are not limited to, oils, nonionic surfactants, amphoteric surfactants, fragrances, dyes, thickeners, hydrotropes, foam stabilizers, solubilizers, preservatives, water softening agents, acids, alkalis, buffers, and the like. Likewise, the compositions can include other emulsifiers, conditioning agents, inorganic salts, humectants, and similar materials to provide the composition with desirable esthetic or physical properties. These optional components and additives usually are present in weight percentages of 0% to about 5% by weight each, and about 0.1% to about 20% by weight of the composition in total.

To improve the conditioning properties of the body wash composition, the composition optionally can include 0% to about 4%, and preferably 0% to about 3%, of an oil. To achieve the full advantages of the present invention, the composition optionally includes 0% to about 2% by weight of an oil. Above about 4% by weight of an oil, the ability of the body wash composition to generate foam is adversely affected, which, in turn, adversely affects the esthetics and consumer acceptance of the composition. Persons skilled in the art are capable of selecting a particular oil, and a particular amount of oil, such that the odor of the composition is not adversely affected.

Examples of oils that can be included in the body wash composition include, but are not limited to, apricot kernel oil, avocado oil, $C_{30-46}$ piscine oil, castor oil, chaulmoogra oil, cherry pit oil, coconut oil, corn oil, cottonseed oil, egg oil, ethiodized oil, grape seed oil, hazel nut oil, hybrid safflower oil, lanolin oil, linseed oil, menhaden oil, mink oil, moringa oil, neatsfoot oil, olive husk oil, olive oil, palm kernel oil, palm oil, peach kernel oil, peanut oil, pengawar djambi oil, rapeseed oil, rice bran oil, safflower oil, sesame oil, soybean oil, sunflower seed oil, sweet almond oil, walnut oil, wheat germ oil, cod liver oil, hydrogenated castor oil, hydrogenated coconut oil, hydrogenated cottonseed oil, hydrogenated jojoba oil, hydrogenated menhaden oil, hydrogenated palm kernel oil, white petrolatum, hydrogenated palm oil, hydrogenated peanut oil, hydrogenated shark liver oil, hydrogenated soybean oil, hydrogenated vegetable oil, jojoba oil, shark liver oil, synthetic jojoba oil, tall oil, vegetable oil, bay oil, cottonseed oil, PEG-2 castor oil, PEG-3 castor oil, PEG-4 castor oil, PEG-5 castor oil, PEG-8 castor oil, PEG-9 castor oil, PEG-10 castor oil, isobutylated lanolin oil, and mixtures thereof.

In addition, to improve skin mildness and composition esthetics, the body wash composition optionally can include an amphoteric surfactant in an amount of 0% to about 5% by weight of the composition. Examples of amphoteric surfactants that can be included in the body wash composition are, but are not limited to, betaines, hydroxypropylsultaines, amine oxides, n-alkylaminopropionates, n-alkylimino dipropionates, phosphobetaines, phosphitaines, imidazolines, and mixtures thereof. Examples of specific amphoteric surfactants include, but are not limited to, cocamidopropyl betaine, lauramidopropyl betaine, coco/oleamidopropyl betaine, coco betaine, oleyl betaine, cocamidopropyl hydroxysultaine, tallowamidopropyl hydroxysultaine, dihydroxyethyl tallow glycinate, cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl)carboxymethylbetaine, oleyldimethylgammacarboxypropylbetaine, lauryl-bis-(2-hydroxypropyl)-carboxyethylbetaine, cocodimethylpropylsultaine, stearyldimethylpropylsultaine, laurylbis-(2-hydroxyethyl) propylsultaine, cocoamidodimethylpropylsultaine, stearylamidodimethylpropylsultaine, laurylamido-bis-(2-hydroxyethyl) propylsultaine, cocamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, lauric myristic amido propyl monosodium phosphitaine, and mixtures thereof. Particularly useful amphoteric surfactants are cocamidopropyl betaine, sold commercially under the brandnames TEGO-BETAINE L10 and TEGO-BETAINE L7, by Goldschmidt Chemical Corp., Hopewell, Va., and cocamidopropyl hydroxysultaine, sold commercially under the brand name VARION CAS, Sherex Chemical Co., Dublin, O. In general, however, any amphoteric surfactant can be included in the composition of the present invention as long as the stability, the conditioning, and the cleansing efficiency of the composition are not adversely affected.

The body wash compositions of the present invention also can include nonionic surfactants to help impart esthetic, physical, or cleansing properties to the composition. For example, representative nonionic surfactants that can be included in the body wash composition of the present invention include esters of polyols and sugars, fatty acid alkanolamides, ethoxylated or propoxylated alkylphenols, ethoxylated or propoxylated fatty alcohols, and the condensation products of ethylene oxide with long chain amines or amides. These nonionic surfactants, as well as numerous others not cited herein, are well known in the art and are fully described in the literature, such as McCUTCHEON'S, DETERGENTS AND EMULSIFIERS, 1993 Annuals, published by McCutcheon Division, MC Publishing Co., Glen Rock, N.J. at pages 266–272, incorporated herein by reference.

In particular, a nonionic alkanolamide can be included in the composition to provide composition thickening and foam stability. The alkanolamide can be included in an amount of 0% to about 10% by weight of the composition. Examples of alkanolamides include, but are not limited to, those known in the art of skin care formulations, such as cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA, and mixtures thereof.

The carrier of the body wash compositions of the present invention is predominantly water, but nonaqueous solvents also can be included to help solubilize composition ingredients that are not sufficiently soluble in water, to adjust the viscosity of the composition, or to act as a humectant. Suitable solvents include polyols, like glycerol, glycols, like ethylene glycol, propylene glycol, and hexylene glycol, or mixtures thereof. The optional nonaqueous solvents should not adversely affect the ability of the composition to cleanse and condition the skin or adversely affect consumer appeal of the composition. A nonaqueous solvent typically is present in a body wash composition in an amount of 0% to about 5% by weight of the composition.

To achieve the full advantage of the present invention, the body wash composition is a relatively viscous mixture, (i.e., a viscosity of about 2,000 to about 20,000 centipoise at 25° C.). A sufficiently viscous body wash composition results from a judicious selection of anionic surfactant, polymeric cationic conditioning compound, quaternized phosphate ester, and desired optional ingredients.

A composition of the present invention often is an emulsion that is stable and that resists phase separation or precipitation of composition ingredients at a temperature of about 20° C. to about 25° C. essentially indefinitely. The compositions also have demonstrated sufficient stability to resist phase separation or precipitation of ingredients at temperatures normally found in commercial product storage and shipping to remain unaffected for periods of one year or more.

In accordance with the method of the present invention, several body wash compositions were prepared, then used to cleanse the skin, to demonstrate the ability of a single application of a composition comprising an anionic cleansing surfactant, a polymeric cationic conditioning compound, and quaternized phosphate ester to simultaneously cleanse and impart conditioning properties to the skin. Although the mechanism of interaction between the essential ingredients that provides a relatively stable composition and allows a maximum deposition of conditioning compounds on the skin is not known precisely, it has been theorized that complexes formed during the manufacture of the composition effectively isolate the cationic quaternary ammonium functionalities from contact with the anionic surfactants.

Consequently, because contact between the anionic and cationic components of the composition is effectively prevented, the cationic components are not precipitated from the composition, do not otherwise interact with the anionic surfactant leading to decreased effectiveness, and, therefore, are available to effectively deposit onto and condition the skin. Similarly, the anionic surfactant also is available to effectively cleanse the skin. Furthermore, and as will be demonstrated more fully hereinafter, tests have demonstrated that a stable and sufficiently high foam level is generated during washing, thereby providing enhanced consumer appeal. Sensory tests have demonstrated that excellent conditioning properties are imparted to the skin.

To demonstrate the new and unexpected results provided by the body wash composition of the present invention, the following Examples 1 through 34 were prepared. The weight percentage listed in each of the following examples represents the actual, or active, amount of each ingredient present in the body wash composition. The compositions were prepared by blending and heating the ingredients, as understood by those skilled in the art.

In the following examples, references to Blend 1 are directed to a premixed concentrate containing:

| Ingredient | % (by weight) |
|---|---|
| PEG-80 Sorbitan Laurate[1] (70%)[2] | 13.3 |
| Sodium Trideceth Sulfate[3] (30%) | 11.7 |
| PEG-150 Distearate[1] (100%) | 3.0 |
| Cocamidopropyl Hydroxysultaine[4] (50%) | 5.8 |
| Disodium Lauroamphodiacetate[4] (38%) | 3.8 |
| Sodium Laureth-13 Carboxylate[3] (70%) | 1.4 |
| Quaternium-15[5] | 0.1 |
| DMDM Hydantoin[5] | 0.1 |
| Water | q.s. |

[1]nonionic surfactant
[2]percent activity of the ingredient as added to the blend
[3]anionic surfactant
[4]amphoteric surfactant
[5]preservative Blend 1 is 39% by weight active, and contains 13.1% by weight anionic surfactant, 9.6% by weight amphoteric surfactant, and 16.3% by weight nonionic surfactant.

| | EXAMPLES 1–4 | | | |
|---|---|---|---|---|
| Ingredient | EX. 1 | EX. 2 | EX. 3 | EX. 4 |
| Sodium Lauryl Ether Sulfate (2 moles EO)[7] | 12.0[12] | 12.0 | 12.0 | 12.0 |
| Blend 1 | 3.6 | 3.6 | 3.6 | 3.6 |
| Cocamide MEA[1] | 7.0 | 7.0 | 7.0 | 7.0 |
| Preservatives[8] | 0.5 | 0.5 | 0.5 | 0.5 |
| Guar Hydroxypropyltrimonium Chloride[13] | 0.2 | 0.2 | 0.2 | 0.2 |
| Tetrasodium Ethylenediamine Tetraacetic Acid[9] | 0.08 | 0.08 | 0.08 | 0.08 |
| Citric Acid | 0.15 | 0.15 | 0.15 | 0.15 |
| Palmitic Acid | 2.0 | 2.0 | 2.0 | — |
| Myristic Acid | — | — | — | 2.0 |
| Stearamidopropyl Phosphatidyl PG-Dimonium Chloride[10] | 0.4 | 0.4 | 0.4 | 0.4 |
| Cocamidopropyl Hydroxysultaine[11] | 1.9 | 1.9 | 1.9 | 1.9 |
| Titanium Dioxide | 0.2 | 0.2 | 0.2 | 0.2 |
| Glycol Stearate[1] | — | 1.0 | — | — |
| Stearamide MEA[1] | — | — | 2.0 | — |

-continued

| EXAMPLES 1-4 | | | | |
|---|---|---|---|---|
| Ingredient | EX. 1 | EX. 2 | EX. 3 | EX. 4 |
| PEG 150 Distearate[1] | — | — | 1.0 | 1.0 |
| Jojoba Oil | — | — | — | 0.5 |
| Water | q.s. | q.s. | q.s. | q.s. |

[7] added as a 30% active material, EO is ethylene oxide;
[8] a combination of 0.25% methyl paraben, 0.20% DMDM Hydantoin, and 0.05% KATHON CG, available from Rohm and Haas Co., Philadelphia, PA.
[9] added as a 39% active material
[10] PHOSPHOLIPID SV, available from Mona Industries, Paterson, NJ, as a 41.5% active material;
[11] VARION CAS, available from Sherex Chemical Co., Inc., Dublin, O, as a 48% active material;
[12] ammonium lauryl ether sulfate (2 moles EO); and
[13] HI-CARE 1000, available from Rhone-Poulenc, Cranbury, NJ.

The compositions of Examples 1-4 were stable compositions having a pH of about 5.5 to about 6.5 and a viscosity of about 5,000 to about 15,000 cps. The compositions generated a consumer-acceptable foam, effectively cleaned the skin, and left the skin with a soft, conditioned feel.

| EXAMPLES 5-7 | | | |
|---|---|---|---|
| Ingredient | EX. 5 | EX. 6 | EX. 7 |
| Sodium Lauryl Ether Sulfate (2 moles EO)[7] | 13.5 | 13.5 | 13.5 |
| Blend 1 | 1.8 | 1.8 | 1.8 |
| Cocamide MEA[1] | 5.0 | 5.0 | 5.0 |
| Preservatives[8] | 0.5 | 0.5 | 0.5 |
| Guar Hydroxypropyltrimonium Chloride | 0.2 | 0.2 | 0.2 |
| Tetrasodium Ethylenediamine Tetraacetic Acid[9] | 0.08 | 0.08 | 0.08 |
| Citric Acid | 0.15 | 0.15 | 0.15 |
| Myristic Acid | 2.0 | 2.0 | 2.0 |
| Stearamidopropyl Phosphatidyl PG-Dimonium Chloride[10] | 0.4 | 0.4 | 0.4 |
| Cocamidopropyl Hydroxysultaine[11] | 1.9 | 1.9 | 1.9 |
| Titanuim Dioxide | 0.2 | — | 0.2 |
| Glycol Stearate[1] | — | 1.0 | — |
| PEG 150 Distearate[1] | 0.5 | 0.5 | 0.5 |
| White Petrolatum | 0.2 | 0.2 | 0.2 |
| Cetyl/Stearyl Alcohol | — | — | 1.0 |
| Water | q.s. | q.s. | q.s. |

| EXAMPLES 8-10 | | | |
|---|---|---|---|
| Ingredient | EX. 8 | EX. 9 | EX. 10 |
| Sodium Lauryl Ether Sulfate (2 moles EO)[7] | 12.0 | 12.0 | 12.0 |
| Blend 1 | 1.8 | 1.8 | 1.8 |
| Cocamide MEA[1] | 4.5 | 7.0 | 7.0 |
| Preservatives[8] | 0.5 | 0.5 | 0.5 |
| Guar Hydroxypropyltrimonium Chloride[12] | 0.2 | 0.3 | 0.3 |
| Tetrasodium Ethylenediamine Tetraacetic Acid[9] | 0.08 | 0.08 | 0.08 |
| Citric Acid | 0.15 | 0.15 | 0.15 |
| Myristic Acid | 1.8 | 2.0 | 1.8 |
| Stearamidopropyl Phosphatidyl PG-Dimonium Chloride[10] | 0.2 | 0.3 | 0.2 |
| Cocamidopropyl Hydroxysultaine[1] | 1.7 | 1.9 | 1.7 |
| Titanium Dioxide | 0.2 | 0.2 | — |
| Glycol Stearate[1] | — | — | 0.75 |
| Stearamide MEA | 1.8 | 2.0 | 1.8 |
| PEG 150 Distearate[1] | 0.9 | 1.0 | 0.5 |
| Castor Oil | — | 0.5 | — |
| White Petrolatum | 0.2 | — | 0.2 |
| Water | q.s. | q.s. | q.s. |

| EXAMPLES 11-13 | | | |
|---|---|---|---|
| Ingredient | EX. 11 | EX. 12 | EX. 13 |
| Sodium Layryl Ether Sulfate (2 moles EO)[7] | 12.0 | 12.0 | 12.0 |
| Blend 1 | 1.8 | 1.8 | 1.8 |
| Cocamide MEA[1] | 4.5 | 7.0 | 7.0 |
| Preservatives[8] | 0.5 | 0.5 | 0.5 |
| Guar Hydroxypropyltrimonium Chloride[13] | 0.2 | 0.3 | 0.3 |
| Polyquaternium-7[14] | 0.5 | — | — |
| Tetrasodium Ethylenediamine Tetraacetuc Acid[9] | 0.08 | 0.08 | 0.08 |
| Citric Acid | 0.15 | 0.15 | 0.15 |
| Myristic Acid | 1.8 | 2.0 | 1.0 |
| Stearamidopropyl Phosphatidyl PG-Dimonium Chloride[10] | 0.2 | 0.2 | 0.2 |
| Cocamidopropyl Hydroxysultaine[11] | 1.7 | 1.9 | 1.9 |
| Titanium Dioxide | 0.2 | 0.2 | 0.2 |
| Glycol Stearate[1] | 0.7 | — | — |
| Stearamide MEA[1] | 1.8 | 2.0 | 2.0 |
| PEG 150 Distearate[1] | 0.5 | 1.0 | 0.5 |
| White Petrolatum | 0.2 | — | — |
| Sodium Chloride | — | — | 0.2 |
| Water | q.s. | q.s. | q.s. |

[14] available commercially as MERQUAT 550, from CalgonCorp., Pittsburgh, PA.

| EXAMPLES 14-15 | | |
|---|---|---|
| Ingredient | EX. 14 | EX. 15 |
| Sodium Lauryl Ether Sulfate (2 moles EO)[7] | 12.0 | 12.0 |
| Sodium Lauryl Sulfate[15] | 3.3 | 3.3 |
| Cocamide MEA[1] | 5.5 | 5.5 |
| Preservatives[8] | 0.5 | 0.5 |
| Guar Hydroxypropyltrimonium Chloride[13] | 0.3 | 0.3 |
| Tetrasodium Ethylenediamine Tetraacetic Acid[9] | 0.08 | 0.08 |
| Citric Acid | 0.15 | 0.15 |
| Stearamidopropyl Phosphatidyl PG-Dimonium Chloride[10] | 0.2 | 0.2 |
| Cocamidopropyl Hydroxysultaine[11] | 1.7 | 1.7 |
| Glycol Stearate | 0.75 | 0.75 |
| Stearamide MEA[1] | 2.0 | 2.0 |
| PEG 150 Distearate[1] | 0.05 | — |
| Castor Oil | 0.5 | 0.5 |
| Sodium Chloride | 0.01 | — |
| Fragrance | q.s. | — |
| Water | q.s. | q.s. |

[15] added as a 30% active solution.

| EXAMPLES 16-19 | | | | |
|---|---|---|---|---|
| Ingredient | EX. 16 | EX. 17 | EX. 18 | EX. 19 |
| Sodium Lauryl Ether Sulfate (2 moles EO)[7] | 12.0 | 12.0 | 12.0 | 13.5 |
| Blend 1 | — | — | — | 0.7 |

EXAMPLES 16–19

| Ingredient | EX. 16 | EX. 17 | EX. 18 | EX. 19 |
|---|---|---|---|---|
| Sodium Lauryl Sulfate[15] | — | 3.3 | 3.3 | — |
| Disodium Laureth Sulfosuccinate[16] | 3.3 | — | — | — |
| Cocamide MEA[1] | 5.5 | 5.5 | 4.0 | 5.5 |
| Preservatives[8] | 0.5 | 0.5 | 0.5 | 0.5 |
| Guar Hydroxypropyltrimonium Chloride[13] | 0.3 | 0.3 | 0.15 | 0.15 |
| Tetrasodium Ethylenediamine Tetraacetic Acid[9] | 0.08 | 0.08 | 0.08 | 0.08 |
| Citric Acid | 0.15 | 0.15 | 0.15 | 0.15 |
| Stearamidopropyl Phosphatidyl PG-Dimonium Chloride[10] | 0.20 | 0.20 | 0.20 | 0.20 |
| Cocamidopropyl Hydroxysultaine[11] | 1.7 | 1.7 | 1.9 | 1.9 |
| Cetyl Palmitate | — | — | — | 0.75 |
| Glycol Stearate[1] | 0.75 | 0.75 | 0.75 | — |
| Stearamide MEA[1] | 2.0 | 2.0 | 2.0 | 2.0 |
| PEG 150 Distearate[1] | 0.3 | 0.2 | 0.25 | 0.20 |
| Sodium Chloride | — | — | 0.2 | 0.01 |
| Fragrance | — | — | q.s. | q.s. |
| Castor Oil | 0.5 | 0.5 | 0.5 | 0.5 |
| Water | q.s. | q.s. | q.s. | q.s. |

[16]added as a 30% active material.

EXAMPLES 20–22

| Ingredient | EX. 20 | EX. 21 | EX. 22 |
|---|---|---|---|
| Sodium Lauryl Ether Sulfate (2 moles EO)[7] | 12.0 | 13.5 | 13.5 |
| Blend 1 | — | 0.7 | 0.7 |
| Sodium Lauryl Sulfate[15] | 3.3 | — | — |
| Cocamide MEA[1] | 5.5 | 5.5 | 4.0 |
| Preservatives[8] | 0.5 | 0.5 | 0.5 |
| Guar Hydroxypropyltrimonium Chloride[13] | 0.15 | 0.30 | 0.15 |
| Tetrasodium Ethylenediamine Tetraacetic Acid[9] | 0.08 | 0.08 | 0.08 |
| Citric Acid | 0.15 | 0.15 | 0.15 |
| Stearamidopropyl Phosphatidyl PG-Dimonium Chloride[10] | 0.20 | 0.20 | 0.20 |
| Cocamidopropyl Hydroxysultaine[11] | 1.9 | 1.9 | 1.9 |
| Glycol Stearate[1] | — | 0.75 | 0.75 |
| Stearamide MEA[1] | 2.0 | 2.0 | 2.0 |
| PEG 150 Distearate[1] | 0.25 | — | — |
| Castor Oil | 0.5 | 0.5 | 0.5 |
| Sodium Chloride | 0.36 | 0.31 | 0.50 |
| Fragrance | q.s. | q.s. | q.s. |
| Hydropropylmethylcellulose | 0.3 | 0.15 | 0.30 |
| Water | q.s. | q.s. | q.s. |

EXAMPLES 23–24

| Ingredient | EX. 23 | EX. 24 |
|---|---|---|
| Sodium Lauryl Ether Sulfate (2 moles EO)[7] | 13.5 | 13.5 |
| Blend 1 | 0.7 | 0.7 |
| Sodium Lauryl Sulfate[15] | — | — |
| Cocamide MEA[1] | 5.5 | 5.5 |
| Preservatives[8] | 0.5 | 0.5 |
| Guar Hydroxypropyltrimonium Chloride[13] | — | — |
| Polyquaternium-10[17] | 0.3 | 0.3 |
| Tetrasodium Ethylenediamine Tetraacetic Acid[9] | 0.08 | 0.08 |
| Citric Acid | 0.15 | 0.15 |
| Stearamidopropyl Phosphatidyl PG-Dimonium Chloride[10] | 0.20 | 0.20 |
| Cocamidopropyl Hydroxysultaine[11] | 1.9 | 1.9 |
| Glycol Stearate[1] | 0.75 | 0.75 |
| Stearamide MEA[1] | 2.0 | 2.0 |
| PEG 150 Distearate[1] | — | 0.20 |
| Castor Oil | 0.5 | 0.5 |
| Sodium Chloride | 0.01 | 0.41 |
| Fragrance | q.s. | q.s. |
| Hydropropylmethylcellulose | 0.15 | 0.30 |
| Water | q.s. | q.s. |

[17]available commercially as UCARE Polymer JP-400, from Amerchol Corp., Edison, NJ.

EXAMPLES 25–27

| Ingredient | EX. 25 | EX. 26 | EX. 27 |
|---|---|---|---|
| Sodium Lauryl Ether Sulfate (2 moles EO)[7] | 13.5 | 13.5 | 13.5 |
| Blend 1 | 0.7 | — | — |
| Sodium Lauryl Sulfate[15] | — | 3.3 | 3.3 |
| Cocamide MEA[1] | 5.5 | 5.5 | 5.5 |
| Preservatives[8] | 0.5 | 0.5 | 0.5 |
| Guar Hydroxypropyltrimonium Chloride[13] | 0.25 | 0.30 | 0.25 |
| Tetrasodium Ethylenediamine Tetraacetic Acid[9] | 0.08 | 0.08 | 0.08 |
| Citric Acid | 0.10 | 0.10 | 0.10 |
| Glycol Stearate[1] | 0.75 | 0.75 | 0.75 |
| PEG 150 Distearate | 0.2 | 0.05 | 0.2 |
| Castor Oil | 2.0 | 2.0 | 2.0 |
| Stearamidopropyl Phosphatidyl PG-Dimonium Chloride[10] | 0.20 | 0.20 | 0.20 |
| Cocamidopropyl Hydroxysultaine[11] | 1.9 | 1.9 | 1.9 |
| Sodium Chloride | 0.31 | 0.31 | 0.31 |
| Fragrance | q.s. | q.s. | q.s. |
| Hydropropylmethylcellulose | 0.15 | 0.15 | 0.15 |
| Water | q.s. | q.s. | q.s. |

EXAMPLES 28–30

| Ingredient | EX. 28 | EX. 29 | EX. 30 |
|---|---|---|---|
| Sodium Lauryl Ether Sulfate (2 moles EO)[7] | 12.0 | 12.0 | 13.5 |
| Sodium Lauryl Sulfate[15] | 3.3 | 3.3 | 3.3 |
| Cocamide MEA[1] | 5.5 | 5.5 | 5.5 |
| Preservatives[8] | 0.5 | 0.5 | 0.5 |
| Guar Hydroxypropyltrimonium Chloride[13] | 0.15 | 0.30 | 0.30 |
| Tetrasodium Ethylenediamine Tetraacetic Acid[9] | 0.08 | 0.08 | 0.08 |
| Glycol Stearate[1] | 0.75 | 1.50 | 0.75 |
| Stearamide MEA[1] | 2.0 | — | — |
| PEG 150 Distearate[1] | 0.25 | 0.05 | — |
| Castor Oil | 0.5 | 1.0 | 4.0 |
| Stearamidopropyl Phosphatidyl PG-Dimonium Chloride[10] | 0.20 | 0.20 | 0.20 |
| Cocamidopropyl Hydroxysultaine[11] | 1.9 | 1.9 | 1.9 |
| Sodium Chloride | 0.18 | 0.31 | 0.31 |
| Fragrance | q.s. | q.s. | — |
| Hydropropylmethylcellulose | 0.03 | 0.15 | 0.15 |
| Water | q.s. | q.s. | q.s. |

The compositions of Examples 1–30 are compositions of the present invention. The compositions were opaque liquids having a viscosity of about 3,500 to about 15,000 cps (centipoise). The compositions of Examples 1–30 exhibited excellent storage stability, showing no phase separation or ingredient precipitation after storage at about 25° C. for several weeks. In contrast, similar compositions that did not include the quaternized phosphate ester demonstrated phase separation after about two weeks storage at 120° F. Accordingly, the quaternized phosphate ester contributes to the stability of the composition, in addition to imparting conditioning properties to the skin, and, therefore, is an essential ingredient.

Other body wash compositions of the present invention can be prepared by varying the identity of ingredients included in the compositions of Examples 1–30. In particular, other anionic surfactants, such as an alpha-olefin sulfonate or a sarcosinate, can be included in the body wash composition without adversely affecting the physical properties, esthetic properties, or the performance properties of the composition. Likewise, an optional betaine can be substituted for the optional alkamidopropyl hydroxysultaine and the physical, esthetic, and performance properties are not adversely affected. As stated previously, varying the identity of the optional alkanolamide also had essentially no effect on either the physical or the performance properties of the composition. Importantly, the other numbers of the PHOSPHOLIPID series of compounds can be substituted for PHOSPHOLIPID SV without adversely affecting the composition.

Some of the compositions of Examples 1–30 were used to cleanse soiled skin. The compositions effectively generated a sufficient lather, cleansed the skin and did not dry out the skin. Sensory tests showed that the body wash composition imparted conditioning properties to the skin, and that the skin felt soft, smooth, and moisturized.

Body wash compositions of the present invention also were subjected to blind tests in which individuals used a body wash composition, then rated the composition. In some tests, the body wash compositions were compared to OIL OF OLAY MOISTURIZING BODY WASH, available from Proctor and Gamble, Cincinnati, O. In these tests, individuals squeezed a small amount of the body wash composition (i.e., about one teaspoonful) onto a wet applicator, like a pouf or a washcloth, worked the composition into a lather on the skin, then rinsed the skin.

The body wash compositions used in these tests were the compositions of Examples 14 and 31–33, illustrated below:

| EXAMPLES 14 and 31–33 | | | | |
|---|---|---|---|---|
| Ingredient | EX. 14 | EX. 31 | EX. 32 | EX. 33 |
| Sodium Lauryl Ether Sulfate (2 moles EO)[7] | 12.0 | 15.0 | 12.0 | 15.0 |
| Blend 1 | — | 0.7 | — | 0.7 |
| Sodium Lauryl Sulfate[15] | 3.3 | — | 3.3 | — |
| Cocamide MEA[1] | 5.5 | 5.5 | 5.5 | 5.5 |
| Preservatives[8] | 0.5 | 0.5 | 0.5 | 0.5 |
| Guar Hydroxypropyltrimonium Chloride[13] | 0.3 | 0.3 | 0.15 | 0.15 |
| Tetrasodium Ethylenediamine Tetraacetic Acid[9] | 0.08 | 0.08 | 0.08 | 0.08 |
| Citric Acid | 0.15 | 0.13 | 0.15 | 0.15 |
| Stearamidopropyl Phosphatidyl PG-Dimonium Chloride[10] | 0.2 | 0.2 | 0.2 | 0.2 |
| Cocamidopropyl Hydroxysultaine[11] | 1.7 | 1.7 | 1.7 | 1.7 |
| Glycol Stearate | 0.75 | 0.75 | 0.75 | 0.75 |
| Stearamide MEA[1] | 2.0 | 2.0 | 2.0 | 2.0 |
| PEG 150 Distearate[1] | 0.05 | — | 0.25 | 0.20 |
| Castor Oil | 0.5 | 0.5 | 0.5 | 0.5 |
| Sodium Chloride | 0.01 | 0.01 | 0.01 | 0.01 |
| Fragrance | q.s. | q.s. | q.s. | q.s. |
| Water | q.s. | q.s. | q.s. | q.s. |

OIL OF OLAY contains an anionic surfactant, soybean oil, an amphoteric surfactant, a nonionic surfactant, polyquaternium-10, and other ingredients. OIL OF OLAY does not contain a quaternized phosphate ester.

In particular, the compositions of Examples 14 and 31 were compared to OIL OF OLAY. OIL OF OLAY is considered a benchmark in the industry, and is the product against which persons in the art compare new products. The test was a blind test conducted using about 425 women of ages 18 through 65 who used a body wash in the three months preceding the test.

In general, the composition of Example 31 received a higher rating than OIL OF OLAY or the composition of Example 14. The composition of Example 31 was milder to the skin and imparted a greater moisturizing after-feel to treated skin. The composition of Example 14 utilized a more aggressive surfactant system, and, therefore, was less mild than the composition of Example 31, but exhibited a superior lathering ability.

Overall, the composition of Example 31 out-performed OIL OF OLAY with respect to moisturizing and cleansing the skin, skin after-feel, and lathering ability. The individuals in the study rated the composition of Example 31 as having a good moisturizing ability, such that the skin felt soft, smooth, and moisturized. The conditioning effects also were durable and long-lasting, thereby obviating the use of a separate skin or body lotion after washing. The composition of Example 31 outperformed OIL OF OLAY with respect to these conditioning attributes, and the composition of Example 14 was comparable to OIL OF OLAY.

With respect to cleansing attributes, the compositions of Examples 14 and 31 performed at least as well as OIL OF OLAY, and left the skin both cleansed and moisturized, with a clean, healthy, and refreshed feeling. With respect to a lathering ability, the composition of Example 31 outperformed, and the composition of Example 14 equalled, OIL OF OLAY. The compositions of Examples 14 and 31 each outperformed OIL OF OLAY with respect to composition viscosity and ease of dispensing.

The comparison tests show that the compositions of Examples 14 and 31 are effective body wash compositions which perform at least as well as an industry benchmark with respect to esthetics, consumer appeal, cleansing, and conditioning. It also should be noted that a body wash composition of the present invention imparts excellent skin conditioning properties even though the composition is free of a silicone or hydrocarbon-based conditioner, which often are included in skin-care compositions to impart conditioning.

The compositions of Examples 32 and 33 also were tested for esthetics, efficacy, and consumer acceptance. In this test, the compositions of Examples 32 and 33 were tested by 73 women of ages 18 through 54 who used a body wash at least once in the three months prior to the test, have normal skin (i.e., is not very sensitive skin), and have neither recent or current skin rashes nor a chronic skin condition. In these tests, each individual used one composition at a time, and the evaluation of one product was completed before testing of the second product was initiated. The individuals used the product normally and without special instructions, and avoided using other body wash compositions during the test period. The test period was seven days in duration, and over 90% of the individuals used the body wash composition four or more times during the seven-day period.

The compositions of Examples 32 and 33 each were rated as acceptable with respect to esthetics and lathering ability. The composition of Example 32 had a higher lathering ability. Overall, the individuals in the test rated the composition of Example 33 as equivalent to their usual brand of body wash.

With respect to application and sensory properties, the compositions of Examples 32 and 33 were easy to disperse and spread, generated a large amount of lather, were easily and completely rinsed, and left the skin exceptionally clean, neither oily nor sticky, but smooth, moisturized, refreshed, and non-irritated. The compositions of Examples 32 and 33 sufficiently moisturized the skin such that the use of a lotion or moisturizer after a bath or shower could be eliminated.

The composition of Example 34 also was prepared. The composition of Example 34 was a stable, clear composition, having a viscosity slightly thicker than water. The composition effectively cleaned and conditioned the skin, without additional conditioning agents such as silicone or hydrocarbon-based conditioners.

Example 34

| Ingredient | % (by weight) |
|---|---|
| Sodium Lauryl Ether Sulfate (2 moles EO)[7] | 12.0 |
| Sodium Lauryl Sulfate[15] | 3.3 |
| Guar Hydroxypropyltrimonium Chloride[13] | 0.3 |
| Stearamidopropyl Phosphatidyl PG-Dimonium Chloride[10] | 0.2 |
| Water | q.s. |

Obviously, many modifications and variations of the invention as hereinbefore set forth can be made without departing from the spirit and scope thereof, and, therefore, only such limitations should be imposed as are indicated by the appended claims.

What is claimed is:

1. A body wash composition comprising:
   (a) about 1% to about 40% by weight of an anionic surfactant;
   (b) about 0.01% to about 2% by weight of a polymeric cationic conditioning compound;
   (c) about 0.01% to about 5% by weight of a quaternized phosphate ester selected from the group consisting of:

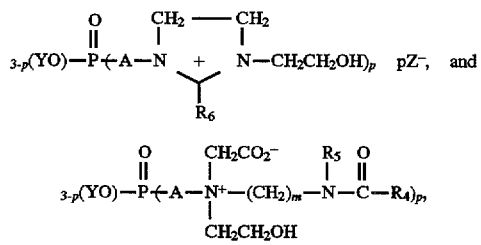

wherein $R_4$ is an aryl, an alkaryl, a saturated alkyl group, an unsaturated alkyl group, a saturated hydroxyalkyl group, or an unsaturated hydroxyalkyl group, wherein the alkyl or hydroxyalkyl group has about 7 to about 21 carbon atoms; $R_5$ is hydrogen, an alkyl group or a hydroxyalkyl group having 1 to about 6 carbon atoms; $R_6$ is an alkyl group having about 5 to about 21 carbon atoms; m is a numeral 1 to about 10; A is a residue of a glycol or a triol having 2 to about 4 carbon atoms; Z is an anion selected from the group consisting of chloride, bromide, methosulfate, ethosulfate, and combinations thereof; Y is selected from the group consisting of hydrogen, an alkyl group, a hydroxyalkyl group, and an aryl group, wherein the alkyl or the hydroxyalkyl group has 1 to about 22 carbon atoms; and p is a numeral 1 to 3; and
   (d) an aqueous carrier.

2. The composition of claim 1 further comprising 0% to about 4% by weight of an oil.

3. The composition of claim 1 further comprising 0% to about 10% by weight of a nonionic surfactant.

4. The composition of claim 1 further comprising 0% to about 5% by weight of an amphoteric surfactant.

5. The composition of claim 1 further comprising 0% to about 4% of an oil, 0% to about 10% of a nonionic surfactant, 0% to about 5% of an amphoteric surfactant, or a mixture thereof.

6. The composition of claim 1 wherein the anionic surfactant comprises an alkali metal salt, an ammonium salt, an alkylammonium salt, or a hydroxyalkylammonium salt, wherein the alkyl group has 1 to about 3 carbon atoms, of an alkyl sulfate, an alkyl ether sulfate, an alkyl ether sulfonate, a sulfate ester of an alkylphenoxy polyoxyethylene ethanol, an alpha-olefin sulfonate, a beta-alkyloxy alkane sulfonate, an alkylarylsulfonate, an alkyl carbonate, an alkyl monoglyceride sulfate, an alkyl monoglyceride sulfonate, an alkyl ether carboxylate, a fatty acid, a sulfosuccinate, a sarcosinate, an octoxynol phosphate, a nonoxynol phosphate, a taurate, a fatty tauride, a fatty acid amido polyoxyethylene sulfate, an isothienate, or mixtures thereof, wherein the fatty moiety has about 12 to about 18 carbon atoms and the alkyl moiety has about 12 to about 18 carbon atoms.

7. The composition of claim 1 wherein the anionic surfactant comprises an alkali metal salt, an ammonium salt, an alkylammonium salt, or a hydroxyalkylammonium salt, wherein the alkyl group has 1 to about 3 carbon atoms, of lauryl sulfate, dodecylbenzenesulfonate, lauryl sulfosuccinate, a lauryl ether sulfate having 1 to about 4 moles of ethylene oxide, a lauryl ether carboxylate having 1 to about 4 moles to ethylene oxide, trideceth sulfate, laureth-13 carboxylate, a laureth sulfosuccinate, lauryl sarcosinate, cocomethyl tauride, a sulfosuccinate half ester amide, and mixtures thereof.

8. The composition of claim 1 wherein the polymeric cationic conditioning compound has an average molecular weight of at least 100,000.

9. The composition of claim 1 wherein the polymeric cationic conditioning compound has an average molecular weight of about 200,000 to about 1,000,000.

10. The composition of claim 1 wherein the polymeric cationic conditioning compound has an average molecular weight of about 250,000 to about 750,000.

11. The composition of claim 1 wherein the polymeric cationic conditioning compound comprises a synthetic quaternized polymer.

12. The composition of claim 11 wherein the synthetic quaternized polymer is selected from the group consisting of polyquaternium-1, polyquaternium-2, polyquaternium-5, polyquaternium-6, polyquaternium-7, polyquaternium-8, polyquaternium-9, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22, polyquaternium-27, polyquaternium-28, polyquaternium-29, polyquaternium-30, and mixtures thereof.

13. The composition of claim 1 wherein the polymeric cationic conditioning compound comprises a naturally derived quaternized polymer.

14. The composition of claim 13 wherein the naturally derived quaternized polymer is selected from the group consisting of polyquaternium-4, polyquaternium-10, polyquaternium-24, guar hydroxypropyltrimonium chloride, guar hydroxypropyltrimonium chloride, cocodimonium hydroxypropyl hydrolyzed rice protein, stearyldimoniumhydroxypropyl hydrolyzed rice protein, hydroxypropyltrimoniumhydrolyzed silk, cocodimonium hydroxypropyl hydrolyzed soy protein, lauryldimonium hydroxypropyl hydrolyzed soy protein, hydroxypropyltrimonium hydrolyzed soy protein, hydroxypropyltrimonium hydrolyzed vegetable protein, stearyldimonium hydroxypropyl hydrolyzed vegetable protein, cocodimonium hydroxypropyl hydrolyzed wheat protein, hydroxypropyltrimonium hydrolyzed wheat protein, stearyldimonium hydroxypropyl hydrolyzed wheat protein, and mixtures thereof.

15. The composition of claim 1 wherein p is 3.

16. The composition of claim 15 wherein the quaternized phosphate ester comprises a fatty $C_8$-$C_{22}$ alkamidopropyl phosphatidyl PG-dimonium chloride.

17. The composition of claim 1 wherein the quaternized phosphate ester has the structure

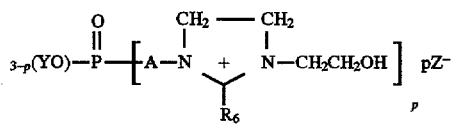

wherein $R_6$ is an alkyl group having about 5 to about 21 carbon atoms; A is a residue of a glycol or a triol having 2 to about 4 carbon atoms; Z is an anion selected from the group consisting of chloride, bromide, methosulfate, ethosulfate, and combinations thereof; Y is selected from the group consisting of hydrogen, an alkyl group, a hydroxyalkyl group, and an aryl group, wherein the alkyl or the hydroxyalkyl group has 1 to about 22 carbon atoms; and p is a numeral 1 to 3.

18. The composition of claim 1 wherein the quaternized phosphate ester has the structure

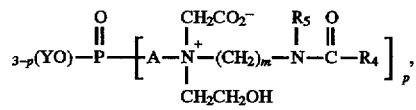

wherein $R_4$ is an aryl, an alkaryl, a saturated alkyl group, an unsaturated alkyl group, a saturated hydroxyalkyl group, or an unsaturated hydroxyalkyl group, wherein the alkyl or hydroxyalkyl group has about 7 to about 21 carbon atoms; $R_5$ is hydrogen, an alkyl group or a hydroxyalkyl group having 1 to about 6 carbon atoms; m is a numeral 1 to about 10; A is a residue of a glycol or a triol having 2 to about 4 carbon atoms; Y is selected from the group consisting of hydrogen, an alkyl group, a hydroxyalkyl group, and an aryl group, wherein the alkyl or the hydroxyalkyl group has 1 to about 22 carbon atoms; and p is a numeral 1 to 3.

19. The composition of claim 1 wherein the quaternized phosphate ester is selected tram the group consisting of stearamidopropyl phosphatidyl PG-dimonium chloride, linoleamidopropyl phosphatidyl PG-dimonium chloride, cocamidopropyl phosphatidyl PG-dimonium chloride, borageamidopropyl phosphatidyl PG-dimonium chloride, laurampho phosphatidyl PG-glycinate, cocohydroxyethyl phosphatidyl PG-imidazolinium chloride, and mixtures thereof.

20. The composition of claim 1 wherein the quaternized phosphate ester is present in an amount of about 0.05% to about 0.5% by weight of the composition.

21. The composition of claim 2 wherein the oil is present in an amount of 0% to about 2% by weight of the composition.

22. The composition of claim 2 wherein the oil is selected from the group consisting of apricot kernel oil, avocado oil, $C_{30-46}$ piscine oil, castor oil, chaulmoogra oil, cherry pit oil, coconut oil, corn oil, cottonseed oil, egg oil, ethiodized oil, grape seed oil, hazel nut oil, hybrid safflower oil, lanolin oil, linseed oil, menhaden oil, mink oil, moringa oil, neatsfoot oil, olive husk oil, olive oil, palm kernel oil, palm oil, peach kernel oil, peanut oil, pengawar djambi oil, rapeseed oil, rice bran oil, safflower oil, sesame oil, soybean oil, sunflower seed oil, sweet almond oil, walnut oil, wheat germ oil, cod liver oil, hydrogenated castor oil, hydrogenated coconut oil, hydrogenated cottonseed oil, hydrogenated jojoba oil, hydrogenated menhaden oil, hydrogenated palm kernel oil, white petrolatum, hydrogenated palm oil, hydrogenated peanut oil, hydrogenated shark liver oil, hydrogenated soybean oil, hydrogenated vegetable oil, jojoba oil, shark liver oil, synthetic jojoba oil, tall oil, vegetable oil, bay oil, cottonseed oil, PEG-2 castor oil, PEG-3 castor oil, PEG-4 castor oil, PEG-5 castor oil, PEG-8 castor oil, PEG-9 castor oil, PEG-10 castor oil, isobutylated lanolin oil, and mixtures thereof.

23. The composition of claim 3 wherein the nonionic surfactant is selected from the group consisting of an ester of a polyol, an ester of a sugar, a fatty acid alkanolamide, an ethoxylated or a propoxylated fatty alcohol, a condensation product of ethylene oxide with a long chain amide, and mixtures thereof.

24. The composition of claim 23 wherein the nonionic surfactant is a fatty alkanolamide selected from the group consisting of cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, and mixtures thereof.

25. The composition of claim 4 wherein the amphoteric surfactant is selected from the group consisting of a betaine, a hydroxypropylsultaine, an amine oxide, and mixtures thereof.

26. The composition of claim 4 wherein the amphoteric surfactant is selected from the group consisting of cocamidopropyl betaine, lauramidopropyl betaine, coco/oleamidopropyl betaine, coco betaine, oleyl betaine, cocamidopropyl hydroxysultaine, tallowamidopropyl hydroxysultaine, and dihydroxyethyl tallow glycinate, and mixtures thereof.

27. The composition of claim 1 wherein the anionic surfactant comprises an alkali metal salt, an ammonium salt, an alkylammonium salt, or a hydroxyalkylammonium salt, wherein the alkyl group has 1 to about 3 carbon atoms, of an alkyl sulfate, an alkyl ether sulfate or a combination thereof; the polymeric cationic conditioning compound comprises guar hydroxypropyltrimonium chloride, polyquaternium-4, polyquaternium-10, polyquaternium-24, or a mixture thereof; the quaternized phosphate ester comprises linoleamidopropyl phosphatidyl PG-dimonium chloride, cocamidopropyl phosphatidyl PG-dimonium chloride, stearamidopropyl phosphatidyl PG-dimonium chloride, or a mixture thereof.

28. The composition of claim 24 further comprising 0% to about 2% of an oil selected from the group consisting of jojoba oil, soybean oil, castor oil, white petrolatum, and mixtures thereof; 0% to about 5% by weight of cocamidopropyl betaine, cocamidopropyl hydroxysultaine, or a mixture thereof; 0% to about 10% by weight of a fatty alkanolamide selected from the group consisting of cocamide MEA, stearamide MEA, and lauramide DEA, or a mixture thereof.

29. A body wash composition comprising:
(a) about 8% to about 30% by weight of an anionic surfactant selected from the group consisting of ammonium lauryl sulfate, sodium lauryl sulfate, ammonium lauryl ether sulfate having 1 to 2 moles of ethylene oxide, sodium lauryl ether sulfate having 1 to 2 moles of ethylene oxide, and mixtures thereof;

(b) about 0.05% to about 0.5% by weight of guar hydroxypropyltrimonium chloride, polyquaternium-4, polyquaternium-10, polyquaternium-24, or a mixture thereof;

(c) about 0.02% to about 0.5% by weight of a quaternized phosphate ester having the structural formula:

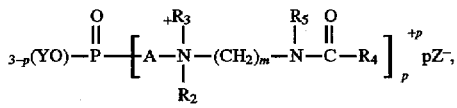

wherein $R_4$ is an aryl group, an alkaryl group, a saturated alkyl group, an unsaturated alkyl group, a saturated hydroxyalkyl group, or an unsaturated hydroxyalkyl group, wherein the alkyl or hydroxyalkyl group has about 7 to about 21 carbon atoms; $R_5$ is hydrogen, or an alkyl or a hydroxyalkyl group having 1 to about 6 carbon atoms; $R_2$ and $R_3$, independently, are an alkyl or a hydroxyalkyl group having 1 to about 6 carbon atoms; A is a residue of a glycol or a triol having 2 to about 4 carbon atoms; Z is an anion selected from the group consisting of chloride, bromide, methosulfate, ethosulfate, and combinations thereof; m is a numeral 1 to about 10; Y is selected from the group consisting of hydrogen, an alkyl group, a hydroxyalkyl group, and an aryl group, either substituted or unsubstituted, wherein the alkyl or the hydroxyalkyl group has 1 to about 22 carbon atoms; and p is a numeral 1 to 3; and (d) 0% to about 2% by weight of an oil selected from the group consisting of soybean oil, castor oil, white petrolatum, jojoba oil, and mixtures thereof;

(e) 0% to about 5% by weight of an amphoteric surfactant selected from the group consisting of cocamidopropyl betaine, lauramidopropyl betaine, coco/oleamidopropyl betaine, coco betaine, oleyl betaine, cocamidopropyl hydroxysultaine, tallowamidopropyl hydroxysultaine, dihydroxyethyl tallow glycinate, and mixtures thereof;

(f) 0% to about 10% by weight of a nonionic alkanolamide selected from the group consisting of cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA, and mixtures thereof; and (g) an aqueous carrier.

30. A method of treating skin to simultaneously cleanse the skin and impart conditioning properties to the skin comprising contacting the skin with a composition comprising:

(a) about 1% to about 40% by weight of an anionic surfactant;

(b) about 0.01% to about 2% by weight of a polymeric cationic conditioning compound;

(c) about 0.01% to about 5% by weight of a quaternized phosphate ester selected from the group consisting of:

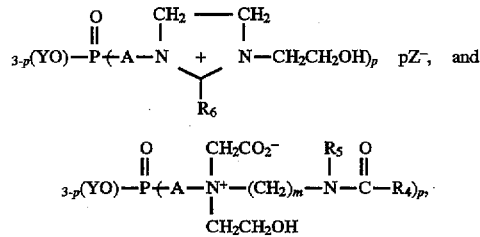

wherein $R_4$ is an aryl, an alkaryl, a saturated alkyl group, an unsaturated alkyl group, a saturated hydroxyalkyl group, or an unsaturated hydroxyalkyl group, wherein the alkyl or hydroxyalkyl group has about 7 to about 21 carbon atoms; $R_5$ is hydrogen, an alkyl group or a hydroxyalkyl group having 1 to about 6 carbon atoms; $R_6$ is an alkyl group having about 5 to about 21 carbon atoms; m is a numeral 1 to about 10; A is a residue of a glycol or a triol having 2 to about 4 carbon atoms; Z is an anion selected from the group consisting of chloride, bromide, methosulfate, ethosulfate, and combinations thereof; Y is selected from the group consisting of hydrogen, an alkyl group, a hydroxyalkyl group, and an aryl group, wherein the alkyl or the hydroxyalkyl group has 1 to about 22 carbon atoms; and p is a numeral 1 to 3; and (d) an aqueous carrier.

* * * * *